United States Patent
D'Angelo

(10) Patent No.: US 9,260,958 B2
(45) Date of Patent: Feb. 16, 2016

(54) SYSTEM AND METHOD FOR ACOUSTIC IMAGING USING A TRANSDUCER ARRAY

(71) Applicant: SCHLUMBERGER TECHNOLOGY CORPORATION, Sugar Land, TX (US)

(72) Inventor: Ralph M. D'Angelo, Weymouth, MA (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 475 days.

(21) Appl. No.: 13/723,143

(22) Filed: Dec. 20, 2012

(65) Prior Publication Data

US 2014/0177388 A1   Jun. 26, 2014

(51) Int. Cl.
G01V 1/44 (2006.01)
G01V 1/40 (2006.01)
G01S 7/524 (2006.01)
E21B 47/00 (2012.01)
E21B 47/09 (2012.01)
E21B 47/10 (2012.01)
G01N 29/06 (2006.01)
G01N 29/26 (2006.01)
G01V 1/02 (2006.01)
E21B 47/08 (2012.01)
G01S 15/89 (2006.01)

(52) U.S. Cl.
CPC ............ *E21B 47/00* (2013.01); *E21B 47/0002* (2013.01); *E21B 47/091* (2013.01); *E21B 47/101* (2013.01); *G01N 29/069* (2013.01); *G01N 29/262* (2013.01); *G01V 1/159* (2013.01); *E21B 47/082* (2013.01); *G01N 2291/106* (2013.01); *G01N 2291/2636* (2013.01); *G01S 7/524* (2013.01); *G01S 15/89* (2013.01); *G01V 1/40* (2013.01); *G01V 1/44* (2013.01); *G01V 2210/1299* (2013.01)

(58) Field of Classification Search
CPC ............ G01V 1/40; G01V 1/44; G01S 7/524; E21B 47/00; E21B 47/082
USPC ................... 367/25, 35, 69, 86; 181/102, 105
See application file for complete search history.

(56) References Cited

U.S. PATENT DOCUMENTS

| | | | |
|---|---|---|---|
| 4,692,908 A | 9/1987 | Ekstrom et al. | |
| 5,044,462 A | 9/1991 | Maki, Jr. | |
| 5,214,251 A * | 5/1993 | Orban et al. | 181/102 |
| 5,469,736 A * | 11/1995 | Moake | 73/152.58 |
| 5,726,951 A | 3/1998 | Birchak et al. | |

(Continued)

OTHER PUBLICATIONS

International Search Report & Written Opinion issued in PCT/US2013/065833 on Mar. 14, 2014; 14 pages.

(Continued)

*Primary Examiner* — Ian J Lobo
(74) *Attorney, Agent, or Firm* — Daniel S. Matthews

(57) ABSTRACT

An apparatus for acoustic imaging includes an array with a number of acoustic transducers. Each acoustic transducer transmits and receives acoustic signals. The apparatus also includes a control unit that is coupled to the array and selectively powers a number of acoustic transducers based upon standoff distance between the array and an object-of-interest (e.g., a borehole wall). In some embodiments, the control unit also varies the frequency of acoustic signals transmitted from the array using the standoff distance between the array and the object-of-interest.

20 Claims, 8 Drawing Sheets

(56) References Cited

U.S. PATENT DOCUMENTS

| | | | |
|---|---|---|---|
| 7,587,936 B2* | 9/2009 | Han | 73/152.43 |
| 8,117,907 B2* | 2/2012 | Han et al. | 73/152.58 |
| 8,194,497 B2* | 6/2012 | Mickael | 367/35 |
| 2004/0200274 A1* | 10/2004 | Moake et al. | 73/152.05 |
| 2005/0068036 A1* | 3/2005 | Wang et al. | 324/338 |
| 2006/0185430 A1 | 8/2006 | Yogeswaren | |
| 2009/0084176 A1* | 4/2009 | Hassan et al. | 73/152.57 |
| 2009/0114472 A1 | 5/2009 | Winkler et al. | |
| 2009/0183941 A1 | 7/2009 | Pabon et al. | |
| 2010/0019771 A1* | 1/2010 | Gold et al. | 324/355 |
| 2010/0023268 A1* | 1/2010 | Gold et al. | 702/9 |
| 2012/0192640 A1 | 8/2012 | Minh et al. | |

OTHER PUBLICATIONS

Morys et al., "Field Testing of an Advanced LWD Imager for Oil-Based Mud Applications," SPWLA 51st Annual Logging Symposium, Jun. 2010: pp. 1-13.

* cited by examiner

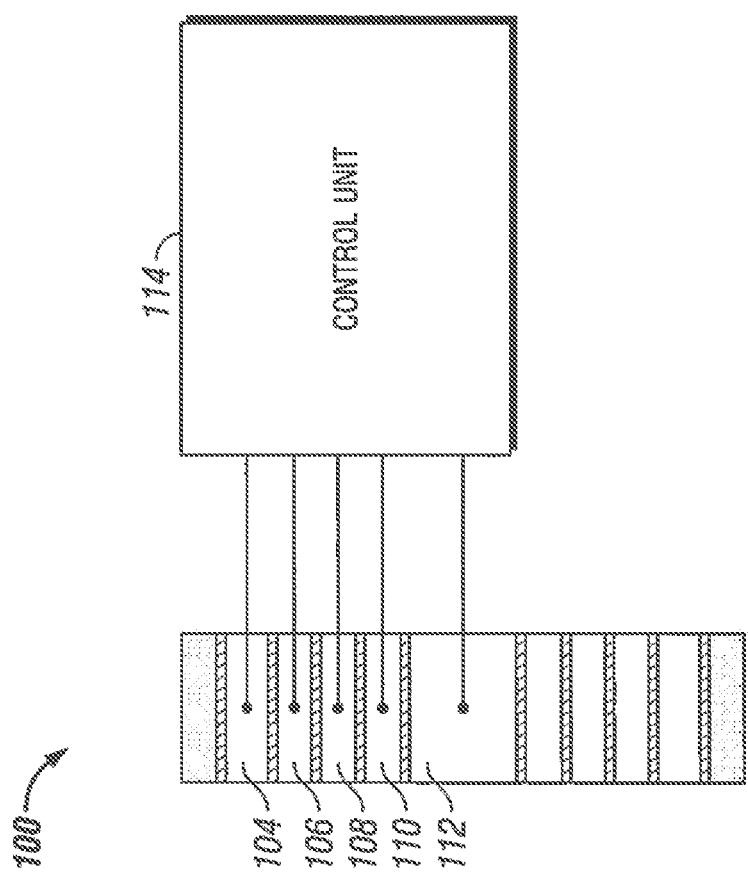
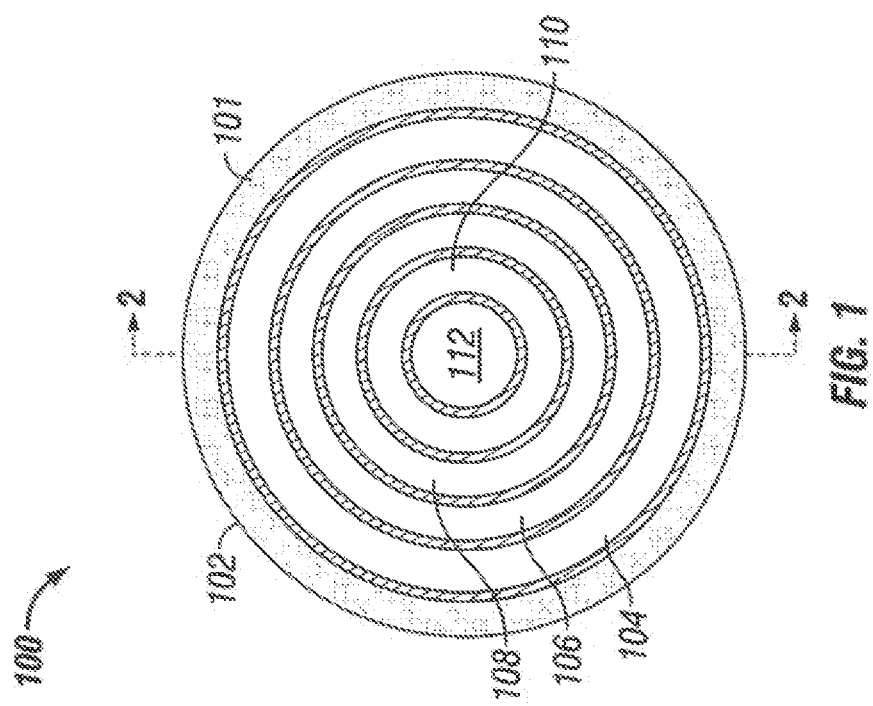
FIG. 1
FIG. 2

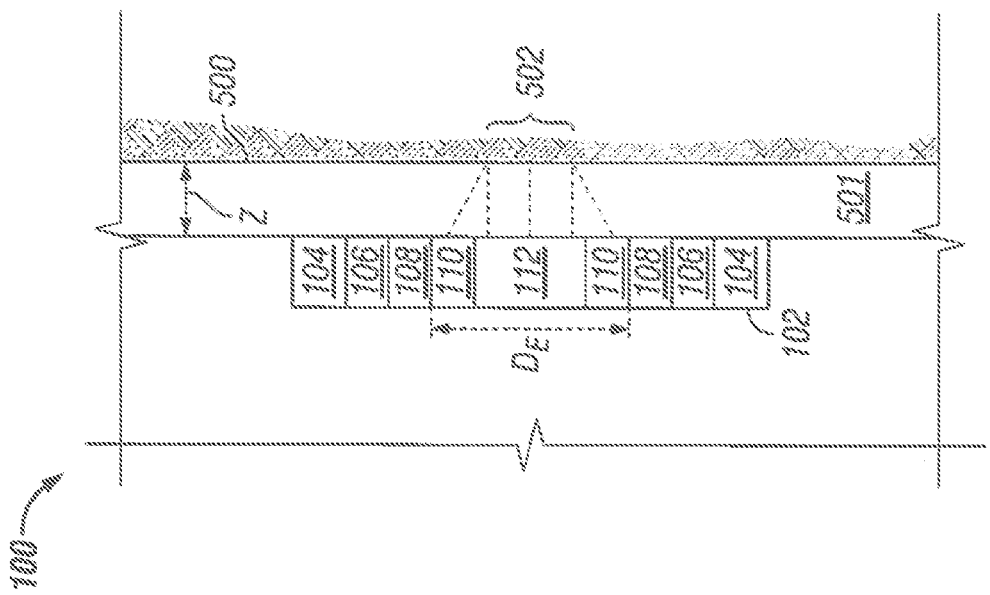
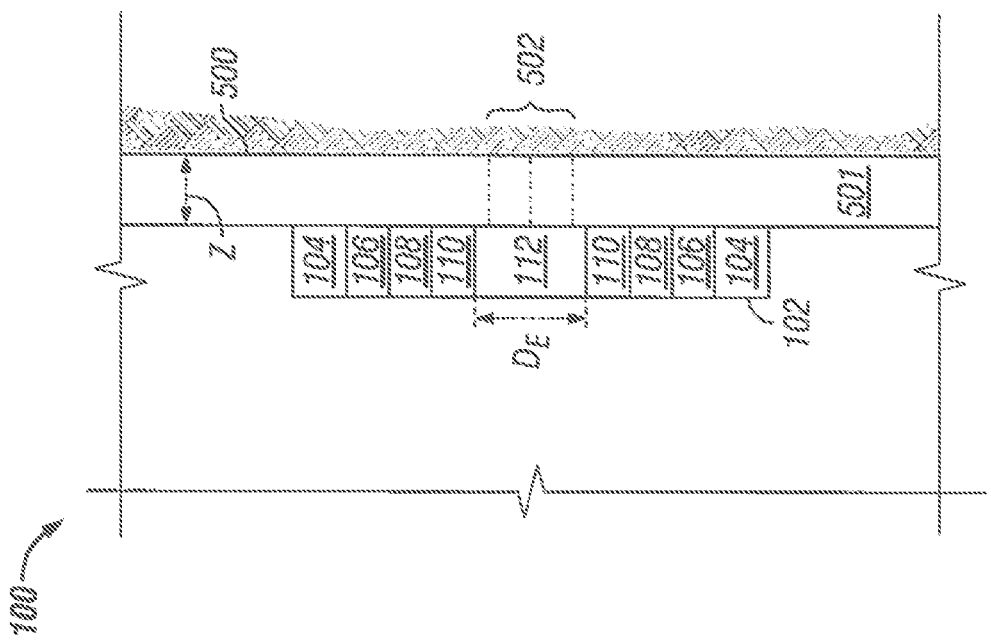

SYSTEM AND METHOD FOR ACOUSTIC IMAGING USING A TRANSDUCER ARRAY

TECHNICAL FIELD

This disclosure relates to system for acoustic imaging, and more particularly to a system for acoustic imaging that uses a transducer array.

BACKGROUND

In the oil and gas industry, subsurface formations are investigated by well logging tools. Such well logging tools can be used to determine formation characteristics. In many cases, acoustic logging tools are used to measure formation acoustic properties, which may be used to derive other characteristics of the formations. For example, acoustic logging tools can be used to image a borehole wall and identify fractures within the borehole wall.

Such acoustic logging tools may include acoustic transducers for transmitting an acoustic signal into a formation and for receiving acoustic signals that return from the formation. The return signal can be used to generate an image of the formation.

A common problem encountered with such acoustic logging tools is that the tools do not adequately focus and image formations at short standoff distances between the borehole wall and the transducer. This is particularly problematic in logging-while-drilling operations where the standoff distance between the drill collar and the borehole wall can be very small.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a borehole tool. The borehole tool includes an array with a number of acoustic transducers. Each acoustic transducer transmits and receives acoustic signals. The borehole tool also includes a control unit that is coupled to the array and selectively powers a number of acoustic transducers based upon standoff distance between the array and a borehole wall. In some embodiments, the control unit also varies the frequency of an acoustic signal transmitted from the array based upon the standoff distance between the array and the borehole wall.

Various embodiments are also directed to a method for acoustically imaging a borehole wall. The method includes disposing an array with a number of acoustic transducers within a borehole. A number of the transducers are selected based upon standoff distance between the array and the borehole wall. The selected acoustic transducers are used to transmit acoustic signals towards the borehole wall.

Illustrative embodiments are further directed to a logging-while-drilling (LWD) tool. The LWD tool includes an array with a number of acoustic transducers. Each acoustic transducer transmits acoustic signals. The LWD tool also includes a control unit that is coupled to the array and configured to (i) selectively power a number of acoustic transducers and (ii) vary a frequency of acoustic signals transmitted from the array based upon standoff distance between the array and a borehole wall.

BRIEF DESCRIPTION OF THE DRAWINGS

Those skilled in the art should more fully appreciate advantages of various embodiments of the disclosure from the following "Description of Illustrative Embodiments," discussed with reference to the drawings summarized immediately below.

FIG. 1 shows an acoustic imaging system in accordance with one embodiment of the present disclosure;

FIG. 2 shows a cross-sectional view of the acoustic imaging system of FIG. 1;

FIG. 5 shows the acoustic imaging system of FIG. 1 in the process of transmitting acoustic signals at a first standoff distance in accordance with one embodiment of the present disclosure;

FIG. 6 shows the acoustic imaging system of FIG. 1 in the process of transmitting acoustic signals at a second standoff distance;

DESCRIPTION OF ILLUSTRATIVE EMBODIMENTS

Figure 3:
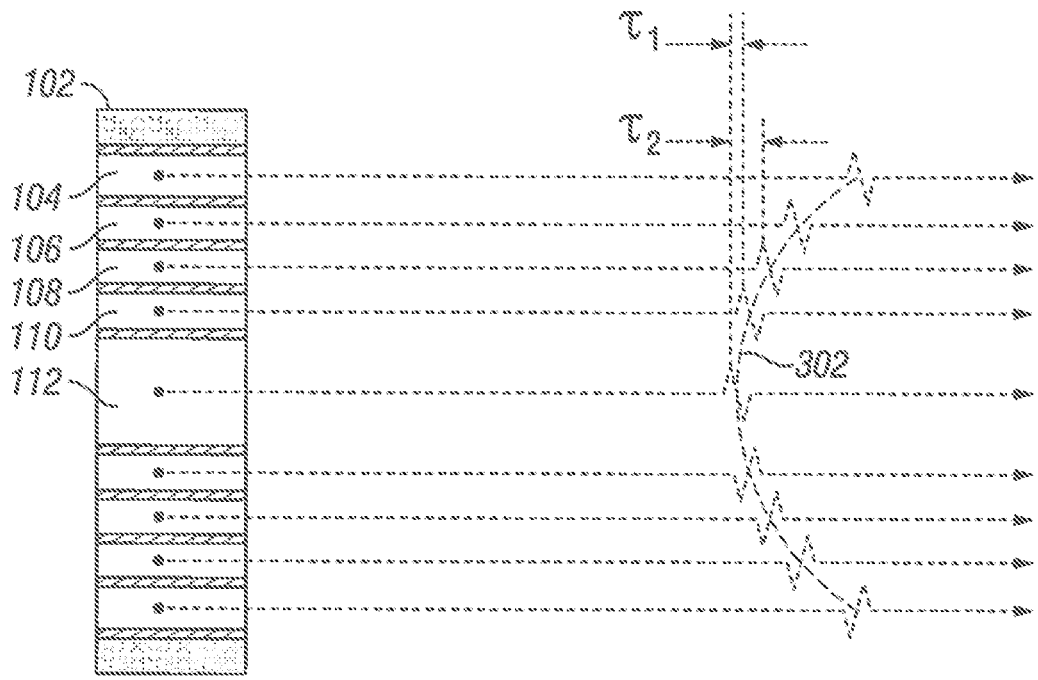
FIG. 3 shows an array of acoustic transducers in the process of transmitting acoustic signals with varied timing in accordance with one embodiment of the present disclosure.

Illustrative embodiments of the present disclosure are directed to an acoustic imaging system for investigating an object-of-interest, such as a borehole wall. In various embodiments, the system is deployed as part of a borehole tool, such as a logging-while-drilling (LWD) tool. The acoustic imaging system includes an array with a plurality of acoustic transducers. Each acoustic transducer transmits and receives acoustic signals. The array is coupled to a control unit, which selectively powers a number of acoustic transducers based upon standoff distance between the array and the borehole wall. In further illustrative embodiments, the control unit also varies the frequency of an acoustic signal transmitted from the array based upon the standoff distance. By selectively powering transducers and varying the frequency of transmitted acoustic signals, exemplary embodiments of the acoustic imaging system maintain focus on the borehole wall for a variety of different standoff distances, while also limiting diffraction and attenuation of the transmitted acoustic signals. Details of various embodiments are discussed below.

FIG. 1 shows an acoustic imaging system 100 in accordance with one embodiment of the present disclosure. The acoustic imaging system 100 includes a housing 101 that includes a transducer array 102 with a plurality of acoustic transducers 104, 106, 108, 110, 112. Each acoustic transducer transmits and receives acoustic signals. As shown in FIG. 1, the array 102 forms a circular area and each of five acoustic transducers form a ring disposed concentrically within the circular area 104, 106, 108, 110, 112. FIG. 2 shows a cross-sectional view of the acoustic imaging system 100. Each of the acoustic transducers is coupled to a control unit 114. The control unit 114 provides an electrical signal to each of the transducers. Each transducer translates the electrical signal into an acoustic signal that travels through a propagation medium, such as borehole fluid. The plurality of transmitted acoustic signals forms an acoustic beam. As the acoustic signals reflect back from an object-of-interest, the acoustic transducers 104, 106, 108, 110, 112 receive the reflected acoustic signals from the medium and translate received acoustic signals into electrical signals. In turn, these electrical signals are communicated to the control unit 114 and used to image the object-of-interest.

In illustrative embodiments of the acoustic imaging system 100, the control unit 114 varies relative timing of each of the transmitted acoustic signals to focus the resultant acoustic beam onto an object-of-interest, such as a borehole wall. FIG. 3 shows the array of acoustic transducers 102 in the process of transmitting acoustic signals with varied timing. To focus the acoustic signals from the transducers onto the object-of-interest, the control unit 114 varies the timing of each of the transmitted acoustic signals. In particular, the control unit 114 advances the timing of the acoustic signals transmitted from the outer transducers relative to the timing of the inner transducers. For example, the timing of the acoustic signal transmitted from the second transducer 110 is advanced by a time difference value ($\tau_1$), as compared to the center transducer 112. Likewise, the timing of the acoustic signal transmitted from the third transducer 108 is advanced by a different time difference value ($\tau_2$), as compared to the timing of the acoustic signal of the center transducer 112. In this manner, each transducer receives its own unique time difference value, relative to the center transducer 112. These unique time difference values are determined based on a chosen profile of the focused beam. In illustrative embodiments, spherical focusing is emulated by the array 102. Therefore, the time difference values chosen provide a beam profile having a spherical curvature, as shown by number 302 in FIG. 3. In other embodiments, the chosen beam profile may have other shapes, such as triangular functions, parabolic functions, or even arbitrary functions.

For spherical focusing, the time difference values are determined based on geometrically translating a linear time axis to a circular axis. The geometric translation uses the standoff distance between the object-of-interest and the center transducer 112 of the transducer array 102. Standoff distance between the center transducer 112 and the object-of-interest can be determined using the acoustic signals transmitted and received from the array, and a value for the velocity of the propagation medium (e.g., borehole fluid). For example, the standoff distance can be determined according to the following relationship:

$$Z = \frac{2c}{T_F} \quad (1)$$

where Z is the standoff distance between the center transducer 112 and the object-of-interest, $T_F$ is the time-of-flight of the acoustic signal, and c is the velocity of the propagation medium (e.g., borehole fluid). In a borehole environment, the transmitted acoustic signal travels to the borehole wall and reflects back to the transducer array 102. The time-of-flight ($T_F$) is measured as the time from when the acoustic signal leaves the transducer 112 to the time when the acoustic signal is detected by the transducer 112. Also, in a borehole environment, the propagation medium is a borehole fluid, such as a drilling mud. In some embodiments, the velocity of the borehole fluid (c) is known based upon the use of a pre-characterized type of drilling mud. In another embodiment, the velocity of the propagation medium is separately measured. The velocity of the propagation medium is directly measured by, for example, a separate module with a known fixed distance between an acoustic source and an acoustic detector. The distance between the source and detector is occupied by the propagation medium under test. U.S. Application Publication No. 2009/0114472, published on May 7, 2009, discloses another method that uses refracted formation signals to determine standoff. One skilled in the art will recognize that there are several other utilized methods for measuring borehole fluid velocity.

In one specific embodiment, the time difference values (TD) of each subsequent transducer (n) along the transducer array 102 can be determined according to the following relationship:

$$TD_n = (\sqrt{Z^2 + X_n^2} - Z)/c \quad (2)$$

where Z is the standoff value between the center transducer 112 and the object-of-interest (e.g., borehole wall), $X_n$ is the distance along the array 102 between a center of transducer element "n" and the center transducer 112, and c is the acoustic velocity of the propagation medium (e.g., borehole fluid). In illustrative embodiments, the transmitted signals from each outer transducer are advanced in time relative to the transmitted acoustic signal of the center transducer 112 by each outer transducer's unique and respective time difference value (TD). In this manner, a beam profile 302 with a relative time distribution pattern is produced, as shown in, for example, FIG. 3.

In additional or alternative embodiments, the acoustic signals are transmitted from the transducer array 102 without any time advance and the time relationship of the acoustic signals that are received at the transducers 104, 106, 108, 110, 112 is varied by the control unit 114. In such an embodiment, the received signals are varied in a similar, but inverse manner from that described above for the transmitted signals. Each signal that is received at a transducer is delayed in time relative to the time at which a signal is received at the center transducer 112. Each signal is delayed by the transducer's unique and respective difference time value (TD). In this manner, focusing of the beam profile is achieved by varying the time relationship of acoustic signals that are received at the transducer array. Various other embodiments could focus the beam by varying both signal transmission timing and signal reception timing.

In illustrative embodiments of the imaging system, the control unit 114 also selectively powers a number of acoustic transducers 104, 106, 108, 110, 112 based upon standoff distance between the transducer array 102 and the object-of-interest (e.g., a borehole wall). In a specific embodiment, the control unit 114 is configured to power the plurality of acoustic transducers 104, 106, 108, 110, 112 such that the number of transducers selectively powered decreases as the standoff distance from the object decreases. For example, at large standoff distances, every transducer 104, 106, 108, 110, 112 of the array 102 is powered by the control unit 114. As the standoff distance decreases, the number of transducers powered decreases so that the transducer array 102 can maintain a small focal spot size on the object at the smaller standoff distances. At small standoff distances from the object, the control unit 114 may power only the center transducer 112, while the outer transducers are not powered (e.g., 110, 108, 106 and 104). In this manner, the transducer array 102 advantageously maintains the small focal spot size on the object at small standoff distances. Maintaining a small focal spot size on the object increases the resolution of the imaging system 100. In contrast, if every transducer was powered at small standoff distances, the effective diameter of the transducer array 102 would become larger than the standoff and the array would fail to focus the object. In some embodiments, the control unit 114 powers the array of transducers according to the following relationship:

$$D_E \leq Z \quad (3)$$

where Z is the standoff distance and $D_E$ is the effective diameter of the imaging array. The effective diameter ($D_E$) is the diameter of the outermost transducer ring that is being powered by the control unit 114. The effective diameter changes as the control unit 114 selectively powers acoustic transducers 104, 106, 108, 110, 112. According to the relationship in Equation 3, the control unit 114 selectively powers the acoustic transducers 104, 106, 108, 110, 112 so that the effective diameter of the acoustic array 102 is less than or equal to the standoff distance.

In illustrative embodiments, the control unit 114 also varies the frequency of acoustic signals transmitted from the transducer array 102 based upon the standoff distance between the array and the object-of-interest (e.g., the borehole wall). In one particular embodiment, as the standoff distance decreases, the frequency of the transmitted acoustic signals increases. In a broadband embodiment, the central frequency of the acoustic array increases. The frequency of the signal is increased because, at low frequencies and at a small effective diameter ($D_E$) of the transducer array 102, the transmitted acoustic signals will diffract considerably within the propagation medium and thus decrease imaging resolution. The amount of diffraction will depend on whether the focal spot of the transducer array 102 is within the near-field zone of the array (e.g., also known as the Fresnal zone). In the near-field zone of transducer array 102, the shape and diameter of the acoustic beam (e.g., the plurality of transmitted acoustic signals) is primarily controlled by the effective diameter ($D_E$) of the array and the selection of time difference values across the transducers of the array (e.g., which determines the degree of focus or curvature of the beam). As the acoustic beam moves away from the transducer array 102 and the beam enters the far-field zone, the beam shape and diameter begin to expand due to diffraction within the medium.

In various embodiments, the control unit 114 adjusts the frequency of the transmitted acoustic signals so that the focal spot of the beam is maintained within the near-field zone. In this manner, the acoustic imaging system 100 preserves the focus of the beam. The length of the near-field zone (e.g., distance from the array to the end of the near-field zone) can be determined according to Equation 4 below:

$$\text{Near Field Length} = \frac{D_E^2 f}{4c} \quad (4)$$

where $D_E$ is the effective diameter of the array, f is the central frequency of the acoustic signal, and c is the velocity of the medium (e.g., velocity of a borehole fluid). In various embodiments, the control unit 114 selectively powers the transducer array 102 so that the array has the largest possible effective diameter ($D_E$). To this end, the control unit 114 uses the standoff distance (e.g., calculated from Equation 1) and the largest allowable effective diameter (e.g., calculated from Equation 3) to select the number of transducers that are powered. The diameter of the outermost transducer that is powered by the control unit 114 is the effective diameter ($D_E$). This value for the effective diameter can be used to solve Equation 5 below to determine a potential frequency range for the transmitted signal.

$$f \geq \frac{4cZ}{D_E^2} \quad (5)$$

Equation 5 shows that the potential frequency range has a lower limit, but the range is not bound by an upper limit. In various embodiments, the control unit 114 selects one frequency value within the range (e.g., at the lower limit) and uses this frequency value to power the transducer array 102. In some embodiments, however, the usable frequency range of the transmitted acoustic signal will also depend on the attenuation characteristics of the propagation medium.

In illustrative embodiments, the control unit 114 selects a frequency value based on both the standoff distance and the attenuation characteristics of the particular propagation medium. As explained above, in a borehole environment, the propagation medium is a borehole fluid, such as a drilling mud. In many cases, drilling muds significantly attenuate high frequency acoustic signals. In some embodiments, the control unit 114 selects the frequency value so that the focal spot falls within the near field zone (e.g., the lower limit calculated according to Equation 5) and also so that the selected frequency produces a measurable acoustic signal at the transducer array 102. The control unit 114 can determine the appropriate frequency by comparing an attenuation loss function for the propagation medium with a signal threshold function for the imaging system 100. The attenuation loss function defines the strength of the acoustic signal received at the acoustic transducer (e.g., amplitude) as a function frequency. In one embodiment, the attenuation loss function is determined by subtracting the total attenuation loss within the propagation medium from an initial strength of the acoustic signal. The initial strength of the acoustic signal can be determined from a prior characterization of the transducer array transfer function within the propagation medium. In various embodiments, the total two-way loss from the transducer array 102 to the borehole wall and back (e.g., twice the standoff distance) is subtracted from the initial signal strength. On the other hand, the signal threshold function defines a minimum signal strength (e.g., minimum amplitude) as a function of frequency that is detectable and measurable by the imaging system 100. In some embodiments, the minimum signal strength is defined as the noise floor for the imaging system 100. These two functions (e.g., attenuation loss function and signal threshold function) can be recorded as equations or look-up tables and provided to, or generated by, the control unit 114. The control unit 114 compares these two functions to determine frequencies (e.g., a range of frequencies or a number of frequencies) at which the functions overlap. The functions will overlap where minimum signal strength is less than the strength of the acoustic signal received at the transducer array 102. Accordingly, in various embodiments, the control unit 114 selects the frequency value based on two conditions. The first condition is that the frequency value produces a focal spot that falls within the near field zone (e.g., the lower limit calculated according to Equation 5) and the second condition is that that the frequency produces a measurable acoustic signal at the transducer array 102 (e.g., frequency values where the attenuation loss and signal threshold functions overlap). In cases where a range of frequencies or a number of frequencies meet both conditions, the control unit 114 may select the highest frequency value for powering the transducer array 102. In cases where the second condition is not met by any frequency values, the control unit 114 may select the frequency value at the lower limit (e.g., according to Equation 5) for powering the transducer array 102.

Figure 4:
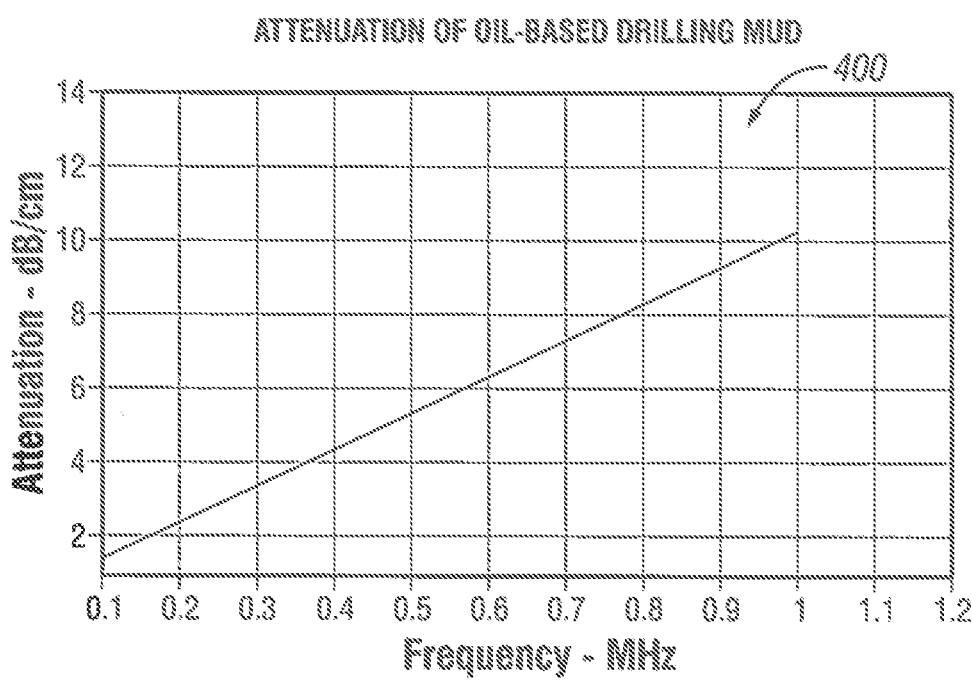
FIG. 4 shows a plot of attenuation versus frequency for a specific oil-based drilling mud.

The attenuation loss function for the propagation medium (e.g., borehole fluid) can be determined a number of different ways. For example, in some cases, the attenuation characteristics of the propagation medium are known based upon, for example, a known type of drilling mud that is being used in a drilling operation. FIG. 4 shows a plot 400 of attenuation versus frequency for a specific oil-based drilling mud. The information within this plot 400 can be provided to the control unit 114 as an equation or a look-up table. This information can be used to determine the attenuation loss function by calculating the total attenuation loss from the transducer array to the borehole wall and back (e.g., twice the standoff distance) and subtracting the total attenuation loss from an initial signal strength. As explained above, the initial strength of the acoustic signal can be determined from a prior characterization of the transducer array transfer function within the propagation medium.

In another embodiment, the attenuation characteristics of the propagation medium are directly measured by a separate module. In one such embodiment, the imaging system 100 includes a separate module with an acoustic source and two acoustic detectors that are separated from the source at different distances. The distances between the source and the detectors are occupied by the propagation medium under test. A signal amplitude difference between the signals received at the two receivers and a known separation distance between the two receivers can be used to determine the attenuation characteristics of the propagation medium at a variety of different frequencies.

In yet another embodiment, the attenuation characteristics of the propagation medium are measured using the transducer array 102 of the imaging system 100. To this end, the control unit 114 analyzes a frequency power spectrum for acoustic signals that propagate through the propagation medium and that are received at the center transducer 112. The frequency power spectrum that is received by the center transducer 112 defines attenuation losses and transmission losses over a range of frequencies for the acoustic signal. The frequency power spectrum can be used by the control unit to determine the attenuation loss function, which is compared against the signal threshold function. In such an embodiment, the control unit 114 can obtain the frequency power spectrum from an acoustic signal used in a previous measurement at a different measurement location. In an additional or alternative embodiment, the control unit 114 uses at least two acoustic signal transmissions at a measurement location. An initial transmission of the acoustic signal is used to determine the frequency power spectrum. This information is used to select an appropriate frequency value for the measurement location and that appropriate frequency value is used to make the actual measurement using a second transmission. In illustrative embodiments, using the frequency power spectrum as the attenuation loss function is advantageous because the spectrum accounts for both attenuation losses and transmission losses. Accordingly, in such embodiments, the initial strength of the acoustic signal may remain an unknown value and the attenuation loss function can be determined without a prior characterization of the transducer array transfer function within the propagation medium.

In various embodiments, the control unit 114 iteratively receives or iteratively determines a current standoff distance and uses the current standoff distance to re-calculate waveform values for the transmitted acoustic signals. These waveform values include (i) an appropriate number of transducers to select, (ii) time difference values for the transmitted acoustic signals, and/or (iii) frequency for the transmitted acoustic signals. In this manner, the control unit 114 iteratively focuses the acoustic signal beam onto the object-of-interest as the standoff distance and measurement location changes. In one specific embodiment, the control unit 114 calculates the waveform values based on a standoff distance that is determined using a previous acoustic signal transmission for a previous acoustic measurement at an adjacent measurement location. In an additional or alternative embodiment, the control unit 114 makes an acoustic measurement using at least two acoustic signal transmissions at a measurement location. An initial acoustic signal transmission is used to determine the standoff distance. This standoff information is then used to calculate the waveform values for a second acoustic transmission, which is used to make the actual measurement for imaging the object-of-interest.

FIGS. 5-8 show the acoustic imaging system 100 in the process of transmitting acoustic signals at various different standoff distances. The acoustic imaging system 100 includes a transducer array 102 with five annular acoustic transducers 104, 106, 108, 110, 112. The transducer array 102 has an outer diameter of 52 mm (without the housing 101) and each of the four outer annular transducers 106, 108, 110, 112 have a width of 4 mm, while the central transducer 112 has a width of 10 mm. Each kerf between the transducers 104, 106, 108, 110, 112 has a width of 1 mm. In FIG. 5, the transducer array 102 is positioned adjacent to a borehole wall 500 with a small standoff distance (e.g., $Z \leq 5$ mm). At a small standoff distance, the control unit 114 powers only the central transducer 112 and produces an effective array diameter ($D_E$) of 10 mm. Given the small effective diameter, the control unit 114 uses a high frequency to prevent diffraction of the acoustic signal within a borehole fluid 501. In various embodiments, the central frequency of the acoustic signal is between 700 KHz and 1.2 MHz at standoff distances less than 5 mm. By using a high frequency and only a single acoustic transducer 112, the acoustic imaging system 100 generates an acoustic beam with a spot size 502 of approximately 10 mm on the borehole wall 500. In contrast, powering all of the acoustic transducers at such a small standoff distance would result in (i) a much larger spot size and (ii) many artifacts in the acoustic signal that is reflected back from the borehole wall.

Figure 8:
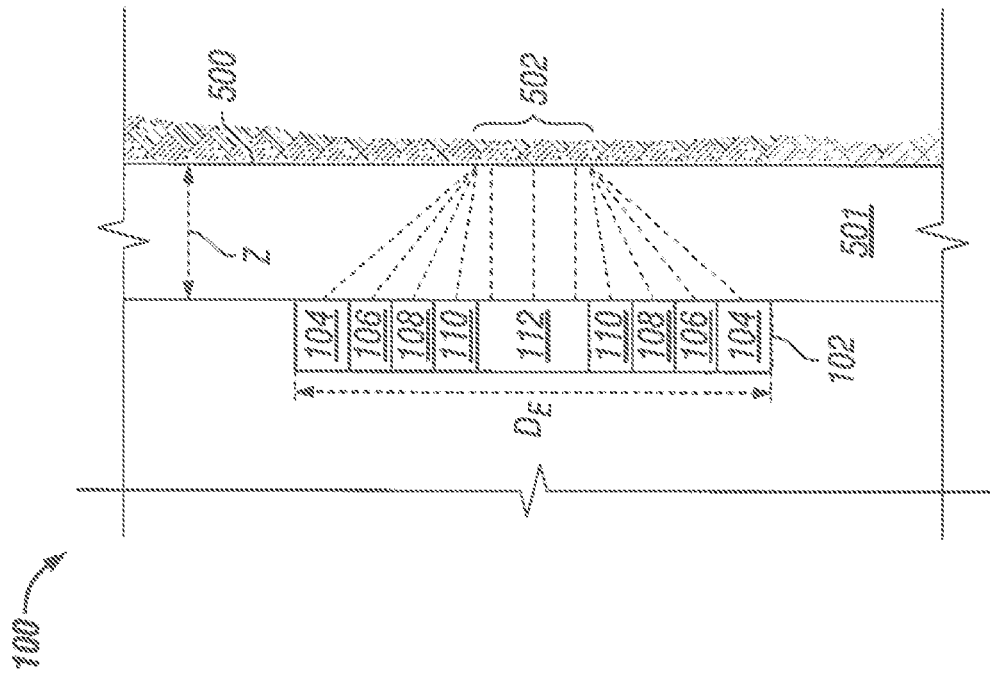
FIG. 8 shows the acoustic imaging system of FIG. 1 in the process of transmitting acoustic signals at a fourth standoff distance.
Figure 7:
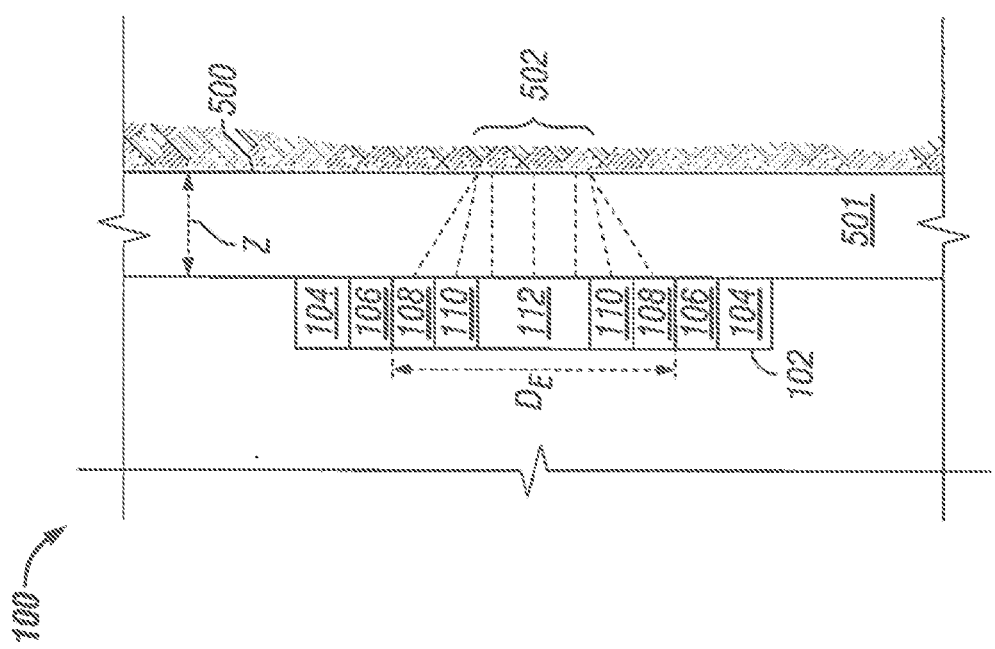
FIG. 7 shows the acoustic imaging system of FIG. 1 in the process of transmitting acoustic signals at a third standoff distance.

As the standoff distance increases, the number of transducers selected increases and the frequency of the transmitted acoustic signal decreases. FIG. 6 shows the acoustic imaging system 100 in the process of transmitting acoustic signals at a different standoff distance (e.g., 5 mm<$Z \leq 15$ mm). At this distance, the control unit 114 powers two inner acoustic transducers 110, 112 and maintains a central frequency between, for example, 500 kHz and 800 kHz. FIG. 7 shows the acoustic imaging system 100 in the process of transmitting acoustic signals at a larger standoff distance (e.g., 15 mm<$Z \leq 30$ mm). The control unit 114 now powers three acoustic transducers 108, 110, 112 and maintains a central frequency between, for example, 350 kHz and 600 kHz. FIG. 8 shows the acoustic imaging system 100 in the process of transmitting acoustic signals at an even larger standoff distance (e.g., $Z > 50$ mm).

The control unit 114 now powers all five acoustic transducers and maintains a central frequency between, for example, 200 kHz and 400 kHz. In each case, the acoustic logging system 100 maintains a focal spot 502 with a spot size of approximately 10 mm on the borehole wall 500. Maintaining a consistent focal spot size helps maintain good resolution over a range of standoff distances.

Figure 9:
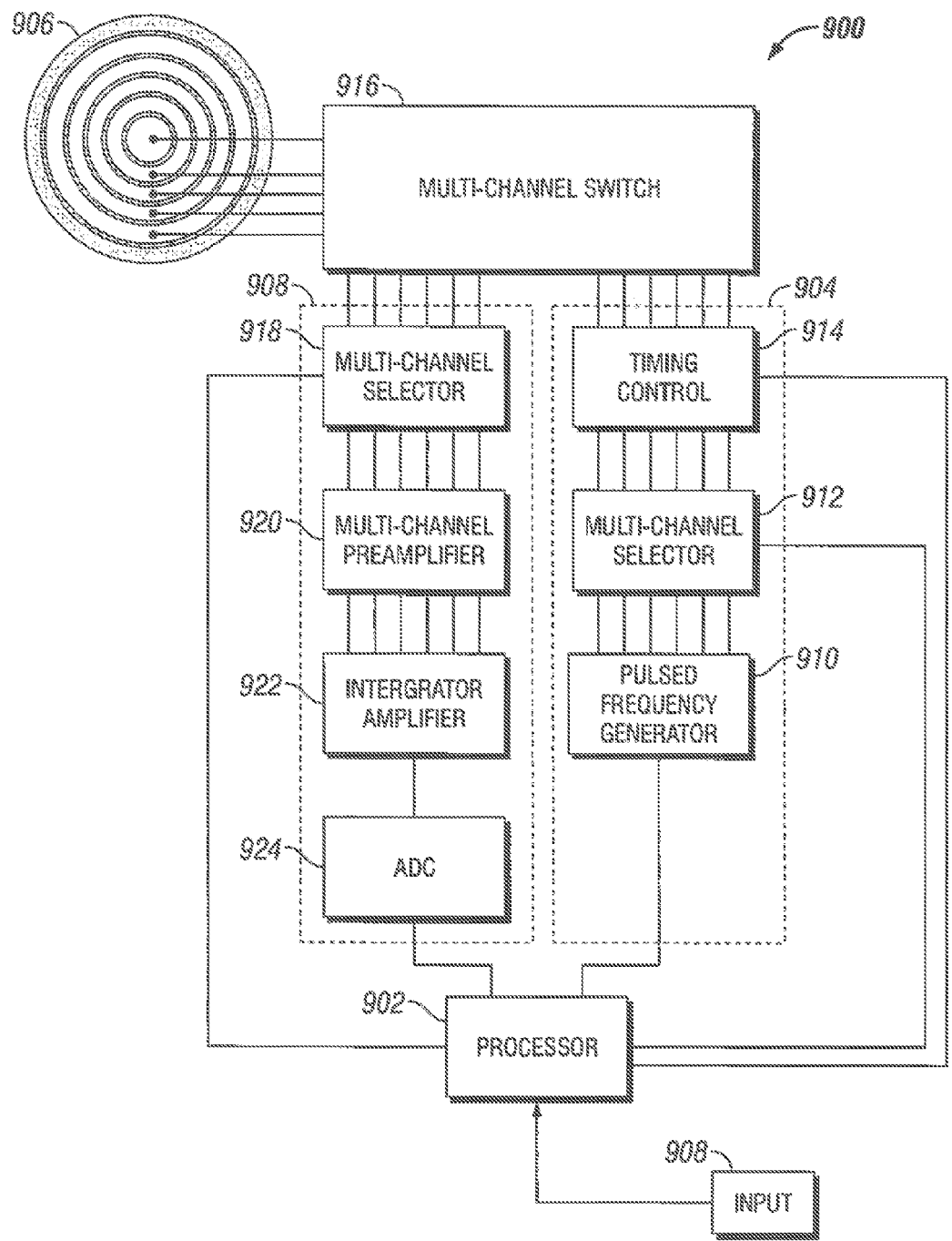
FIG. 9 shows a control unit in accordance with one embodiment of the present disclosure.

FIG. 9 shows a control unit 900 in accordance with one embodiment of the present disclosure. The control unit 900 includes a processor 802, such as a central processing unit (CPU). The processor 902 determines waveform values (e.g., amplitude, timing, transducer selection, and/or frequency) for a pulse waveform that is generated by a transmission module 904 and communicated to a transducer array 904. The processor 902 also supports a receiving module 908 that processes acoustic signals received at the transducer array 906 from an object-of interest. To support the transmission of acoustic signals, illustrative embodiments of the processor 902 determine an appropriate time difference value for each acoustic transducer within the transducer array 906 based upon standoff distance. In this manner, the processor 902 determines an appropriate beam profile for the acoustic signals. Also, the processor 902 determines which acoustic transducers will be powered based upon the standoff distance. This information is output as a channel selection parameter. Furthermore, in various embodiments, the processor 902 determines a frequency for the pulsed waveform based upon the standoff distance. The processor 902 outputs this information as a frequency value. In some embodiments, the processor 902 determines the frequency value of the pulse waveform based upon both the standoff distance and the attenuation of the propagation medium. The processor 902 determines these waveform values using, for example, one or more of Equations 1-5.

The processor 902 may use a variety of different inputs 908 to determine the waveform values. For example, in one embodiment, the standoff distance is pre-calculated and provided to the processor 902. In other embodiment, the processor 902 calculates the standoff itself by determining a time-of-flight for a transmitted acoustic signal and using, for example, the relationship in Equation 1. Also, in various embodiments, the velocity and/or the attenuation characteristics of the propagation medium are provided to the processor as an input 908 (e.g., as a look-up table or as an equation).

These waveform values are provided to the transmission module 904, which powers and controls the acoustic signals generated by the transducer array 906. In particular, the transmission module 904 includes a pulsed-frequency generator 910 that generates the pulsed waveform using at least some of the waveform values. In one embodiment, the frequency value is communicated to the pulsed-frequency generator 910 from the processor 902 and the pulsed-frequency generator generates a waveform with the frequency assigned by the frequency value. In illustrative embodiments, the pulsed waveform is transmitted as an analog signal along a plurality of channels. In some embodiments, the number of channels matches the number of acoustic transducers within the transducer array 906. Each channel is assigned to a particular transducer within the transducer array 906. In this case, the pulsed waveform generator 910 transmits the pulsed waveform along six channels because the transducer array 906 includes six transducers. In an alternative embodiment, a single channel can power multiple transducers.

The transmission module 904 also includes a multi-channel selector 912 that selectively passes the channels. The multi-channel selector 912 is responsible for selectively powering each transducer within the transducer array 906 based upon the channel selection parameter that the selector receives from the processor 902. For example, if the processor 902 determines that three inner transducers should be powered, then those channels will pass the selector 912, while the other three channels are not passed.

The selected channels pass to a timing control 914 that focuses the acoustic signals that are transmitted from the transducer array 906 onto the object-of interest. To this end, the timing control 914 advances the pulsed waveform in at least some of the channels according to the time difference values that the timing control receives from the processor 902.

This pulsed waveform is then passed along the selected channels to a multi-channel switch 916. The multi-channel switch 916 selectively couples the transmission module 904 to the transducer array 906. The multi-channel switch 916 is used to switch between a transmitting mode of operation and a receiving mode of operation. In the transmission mode, the multi-channel switch 916 couples the transmission module 904 to the transducer array 906 and the transmission module provides a high voltage pulsed waveform to the transducer array. At the same time, the switch electrically isolates the receiving module 908 and protects the receiving module from the high voltage pulsed waveform. In the receiving mode, the switch 916 couples the receiving module 908 to the transducer array 906 while decoupling the transmission module 904 from the transducer array 906 and receiving module 908. In doing so, the switch 916 insulates the transducer array 906 and the receiving module 908 from electrical artifacts that may come from the transmission module 904. By switching between operating modes, the multi-channel switch 916 allows the control unit 900 to both transmit acoustic signals from the transducer array 906 and process acoustic signals that are received by the array. In exemplary embodiments, the switch 816 switches from a transmission mode to a receiving mode within 2 microseconds to 8 microseconds after transmission of the acoustic signal and the switch remains in the receiving mode for 2 microseconds to 200 microseconds.

As explained above, the receiving module 908 processes acoustic signals that are received at the transducer array 906 from the object-of-interest so that the acoustic signals can be used for imaging the object. As the acoustic signals reflect back from the object-of-interest, the signals strike the transducer array 906 and are converted by each transducer into analog electrical signals. In the receiving mode of operation, these analog electrical signals pass along the channels and through the multi-channel switch 916 to the receiving module 908.

At the receiving module 908, another multi-channel selector 918 selectively passes the number of channels. In illustrative embodiments, the multi-channel selector 918 selectively passes signals from each transducer based upon the channel selection parameter that the selector receives from the processor 902. In specific embodiments, the multi-channel selector 918 passes signals from the same transducers that are being selectively powered by the transmission module 904.

The receiving module 908 amplifies and integrates the analog signal within each of the channels. To this end, the receiving module 908 includes a multi-channel preamplifier 920 that amplifies the analog signals within each of the channels and an integrator amplifier 922 that integrates each of the channels into a single, integrated analog signal. This integrated analog signal is converted into a digital signal using an analog to digital converter (ADC) 924 and communicated to the processor 902.

The digital signal can be saved to memory and then used to form an image of the object-of-interest. In a specific embodiment, the digital signal is recorded as a function of time (e.g., the digital signal includes time stamp information). The digital signal (e.g., amplitude of the digital signal) at a particular time and position information for the transducer array (e.g., azimuth and standoff distance) at that particular time can be used to recreate an image of the object-of-interest, as is conventionally known in the art.

Illustrative embodiments of the control unit are not limited to the embodiment shown in FIG. 9. In various embodiments, the control unit may include additional components, different components, and/or components arranged in other configurations. For example, in a specific embodiment, the receiving module includes a multi-channel filter that filters the signal within each channel based on the frequency value provided by the processor. In another specific example, the timing control is a component within the receiving module, rather than the transmission module. In such an embodiment, some of the received acoustic signals are delayed according to their respective time difference values. In yet another specific embodiment, the ADC converts the analog signal to a digital signal before pre-amplification and integration. Thus, pre-amplification and integration are performed on a digital signal.

Figure 11:
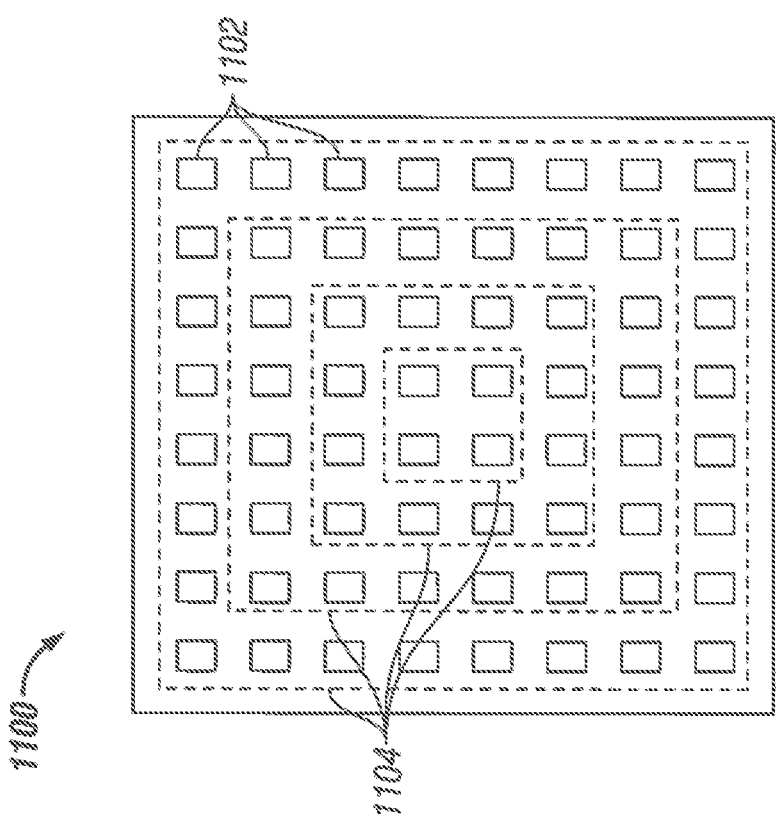
FIG. 11 shows an acoustic array in accordance with another embodiment of the present disclosure.
Figure 10:
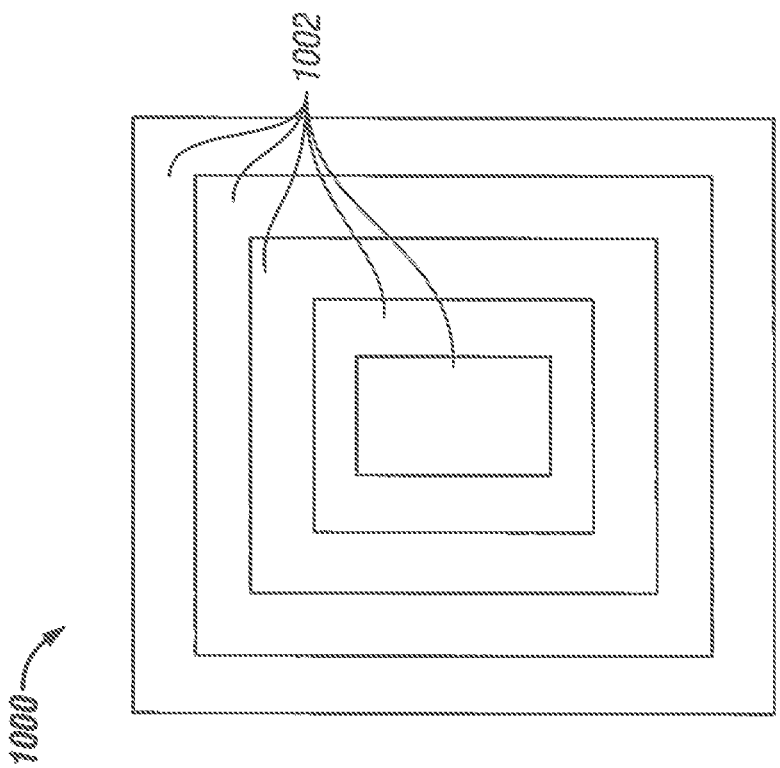
FIG. 10 shows an acoustic array in accordance with one embodiment of the present disclosure.

Illustrative embodiments of the transducer array are also not limited to any particular type of configuration. For example, the transducer array can have a variety of different ring configurations. As shown in FIG. 1, the transducer array 102 can have a circular shape with a plurality of concentric ring transducers 104, 106, 108, 110, 112. Furthermore, in various embodiments, the array has a flat-face design. In additional or alternative embodiments, at least some of the transducers have curved surfaces. For example, in one specific embodiment, the center transducer has a spherical curvature, while the outer transducers have flat-face designs. In illustrative embodiments, the diameter of the transducer array can be between 25 mm and 75 mm and the width of each ring can be between 0.02 mm and 15 mm. In a specific example, the transducer array has a package thickness of about 30 mm (e.g., package has a tungsten-rubber backing of 20 mm). The number of transducers can also vary (e.g., 2, 3, 4, 10, and 20). Furthermore, the transducer array can form a variety of different shapes. For example, FIG. 10 shows an acoustic transducer array 1000 that has a rectangular shape (e.g., square) with a plurality of concentric rectangular transducers 1002. Each of these rectangular transducers is selectively powered by a control unit, as described herein. FIG. 11 shows another transducer array 1100 with a rectangular shape. In this case, the array 1100 includes a plurality of transducers 1102 that are formed by protrusions that extend from a planar surface. These protrusions can be divided into a plurality of concentric sections 1104 that are selectively powered by a control unit.

In illustrative embodiments, each of the transducers within the transducer array is a piezoelectric transducer. The transducer array can be manufactured from a single piece of piezoelectric material by etching or machining trenches (e.g., kerfs) within the material. The trenches define and insulate each transducer. In various embodiments, the transducers are made from a piezo-ceramic material. In additional or alternative embodiments, the transducers are made from a piezo-composite material. In a piezo-composite embodiment, the base of each transducer is formed from a piezo-ceramic material and a thin layer of additional material (e.g., PEEK) is disposed on top of the piezo-ceramic base. The thin layer of additional material improves the transmission of signals between the transducers and the propagation medium by better matching the acoustic impedance of the propagation medium (e.g., commonly known as a matching layer).

Figure 12:
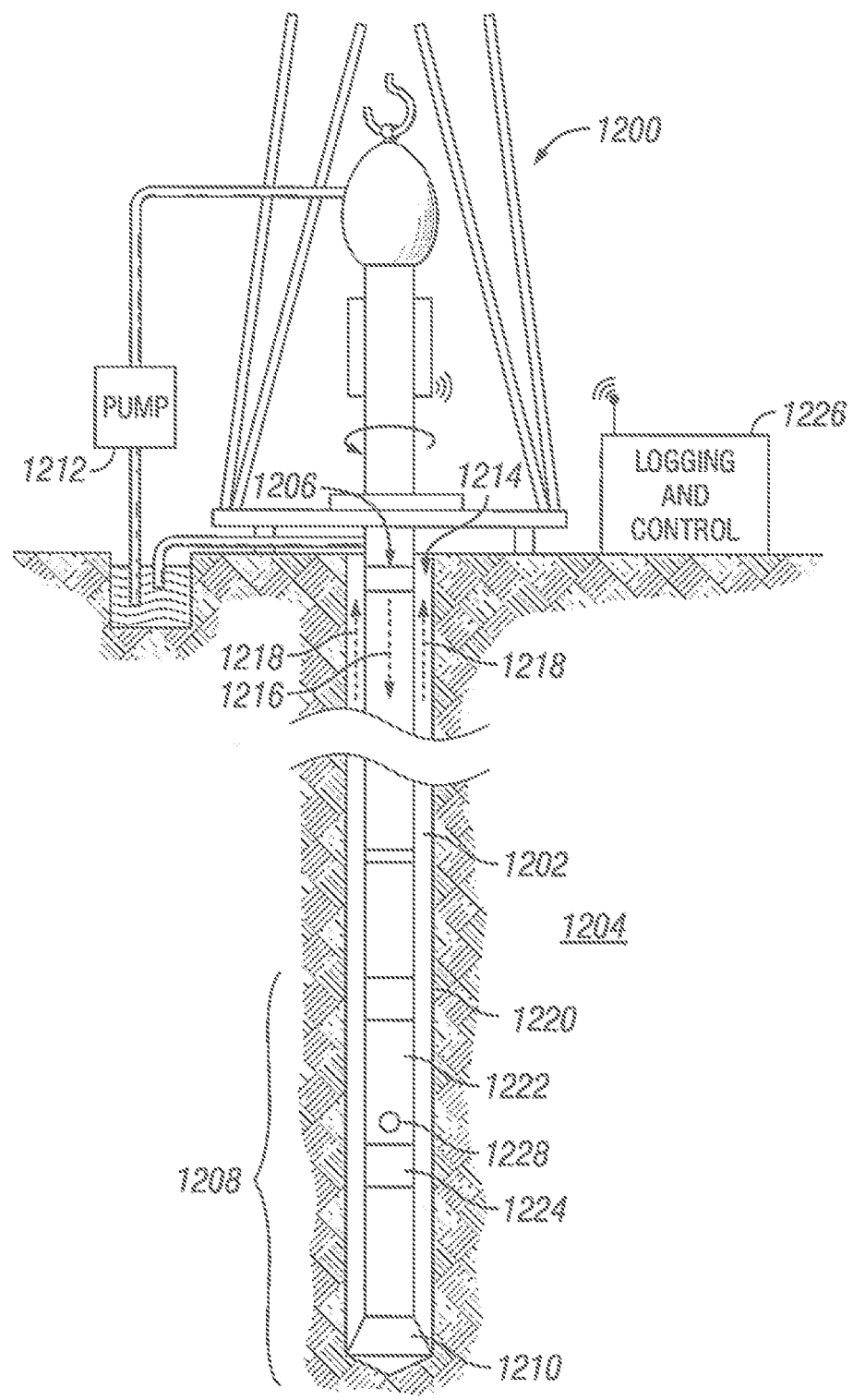
FIG. 12 shows a borehole tool in accordance with one embodiment of the present disclosure.

Illustrative embodiments of the acoustic imaging system have oil field and gas field applications. For example, FIG. 12 shows a wellsite system 1200 that is used to drill a borehole 1202 that traverses a subsurface formation 1204. The wellsite system 1200 includes a drill string 1206 that is suspended within the borehole 1202. The drill string 1206 includes a bottom-hole assembly 1208 with a drill bit 1210 at its lower end. A rotary motion is applied to the drill string 1206 so that the drill bit 1210 can drill further into the formation. The wellsite system 1200 also includes a pump 1212 that circulates a drilling mud 1214 between an interior channel of the drill string 1206, as indicated by direction arrow 1216, and an annulus between a borehole wall 1220 and the drill string 1206, as indicated by directional arrows 1218. The drilling mud 1214 lubricates the drill bit 1210 and carries formation cuttings up to the surface.

In the illustrated example, the bottom-hole assembly 1208 includes a logging-while-drilling (LWD) module 1222 and a measuring-while-drilling (MWD) module 1224. The LWD module 1222 collects information about the characteristics of the formation 1204 (e.g., composition of formation fluids and/or density of the formation). The MWD module 1224 measures physical characteristics of the drill string 1206 and drill bit 1210 (e.g., borehole temperatures, borehole pressures, and wellbore trajectory). Information from the LWD module 1222 and the MWD module 1224 can be communicated to a logging and control module 1226 at the surface of the wellsite 1200 using a telemetry system, such as a mud pulse telemetry system. In turn, the logging and control module 1226 at the surface is used to operate and control the bottom-hole assembly 1208.

In illustrative embodiments, the LWD module 1222 includes an acoustic imaging system, such as the one shown in FIGS. 1 and 2. In a specific embodiment, the LWD module 1222 includes a transducer array 1228 with a plurality of acoustic transducers. The wellsite system 1200 also includes a control unit, such as the one shown in FIG. 9. In illustrative embodiments, the components of the control unit may be located entirely within the bottom-hole assembly 1208 (e.g., within the LWD module 1222), entirely at the surface (e.g., within the logging and control module 1226), or the component may be split between the bottom-hole assembly 1208 and a surface location. As the drill string 1206 rotates, the transducer array 1228 emits acoustic signals to image the borehole wall. As explained above, the control unit selectively powers the transducers based upon standoff distance between the transducer array 1228 and the borehole wall 1220. In various embodiments, the control unit also varies the frequency of the transmitted acoustic signals based upon the standoff distance. The acoustic signals that are reflected from the borehole wall 1220 are received by the transducer array 1228 and processed by the control unit. The LWD module 1222 also tracks the position (e.g., depth and azimuth) of the transducer array 1228 within the borehole 1202. The received acoustic signals and the position information can be used to reconstruct an image of the borehole wall 1220, as is conventionally known. The image of the borehole wall 1220 provides valuable information about the subsurface formation 1204, such as the identification of fractures and different layers within the formation.

Illustrative embodiments of the acoustic imaging system are particularly well suited for operation in LWD applications for at least two reasons. Firstly, in exemplary embodiments, the acoustic imaging system has a reduced size that better fits into a LWD module. In some embodiments, the transducer array includes a flat-face design, such as the one shown in FIG. 2. Such a flat-face design consumes less space than a conventional concave transducer array design. Accordingly, the flat-face design is particularly advantageous for use in a LWD module where available space is scarce. Secondly, the acoustic imaging system advantageously focuses on the borehole wall at small standoff distances. In LWD applications, the standoff distance is small (e.g., less than 12 mm) and the acoustic imaging system described herein can focus on the borehole wall at such small standoff distances by selectively powering acoustic elements within the array and, in some cases, also varying the frequency of the transmitted acoustic signal.

Figure 13:
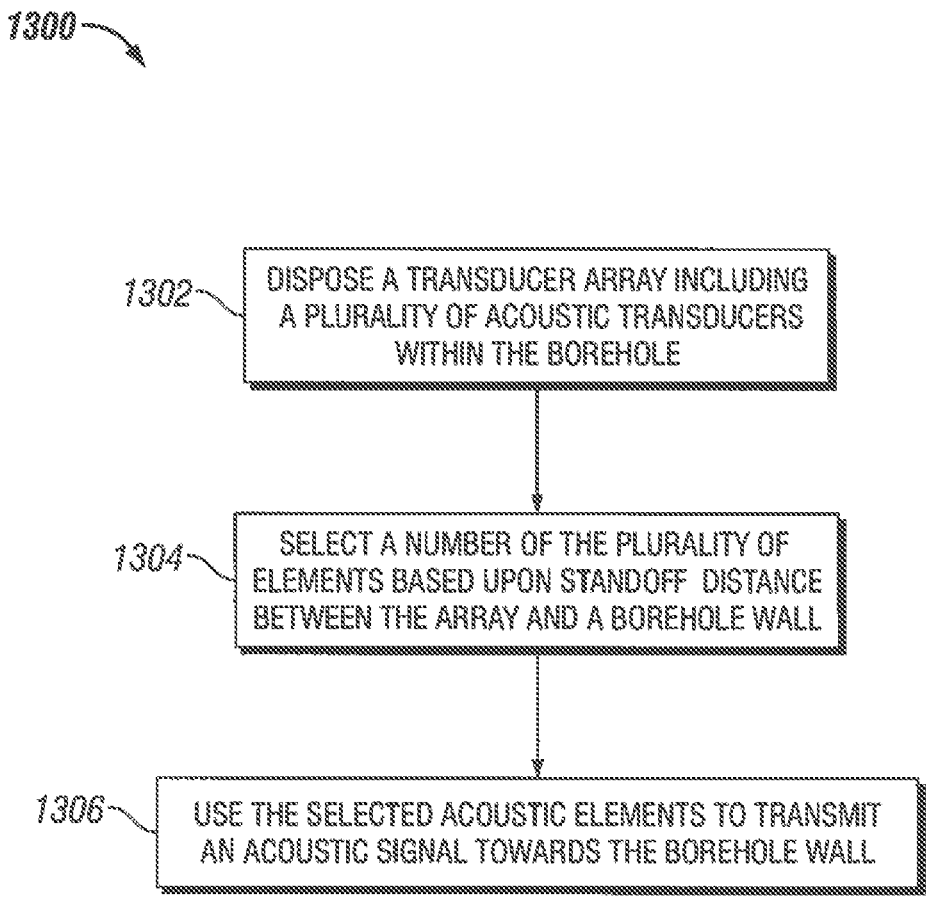
FIG. 13 shows a method for acoustically imaging a borehole wall in accordance with one embodiment of the present disclosure.

Illustrative embodiments of the present disclosure are also directed to methods for acoustically imaging a borehole wall. FIG. 13 shows a simplified method 1300 for acoustically imaging a borehole wall. The method 1300 includes disposing a transducer array within the borehole 1302. For example, the transducer array may be positioned within the borehole to image the borehole wall during a LWD operation. n the specific example shown in FIG. 12, the transducer array is disposed within the borehole as part of an LWD module. The transducer array includes a plurality of acoustic transducers. The method continues to process 1304, which requires selecting a number of the transducers within the borehole based upon standoff distance between the array and a borehole wall. This process is performed by the control unit. In illustrative embodiments, as the standoff distance decreases, the number of acoustic transducers selected decrease and the effective diameter of the array also decreases to better focus the transmitted acoustic signals onto a focal spot on the borehole wall. The acoustic transducers that are selected by the control unit are used to transmit an acoustic signal towards the borehole wall 1306. In an LWD application, the transmitted acoustic signals travel through the drilling mud and reflect from the borehole wall and travel back to the transducer array. The received acoustic signal is processed by the control unit, as described above, and used to image the borehole wall.

Illustrative embodiments of the present disclosure are not limited to LWD applications, such as the one shown in FIG. 12. For example, illustrative embodiments of the acoustic imaging system can also be used within the MWD module. n such an embodiment, information from the acoustic imaging system can be used to control and steer the drill string. Various embodiments of the acoustic imaging system may also be applied in other borehole tools, such as a wireline tool or any other tool deployed within a borehole that uses any suitable means of conveyance, such coiled tubing.

The term "processor" should not be construed to limit the embodiments disclosed herein to any particular device type or system. The processor may include a computer system. The computer system may include a computer processor (e.g., a microprocessor, microcontroller, digital signal processor, or general purpose computer). The computer system may also include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Any of the methods and processes described above, including processes and methods for (1) determining time difference values based upon standoff distance, (2) selectively powering transducers based upon standoff distance (e.g., determining a channel selection parameter), (3) determining a frequency value based upon standoff distance and/or attenuation characteristics, and/or (4) determining standoff distance, can be implemented as computer program logic for use with the computer processor.

The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a computer readable medium (e.g., memory) and executed by the computer processor.

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:

1. A borehole tool comprising:
an array including a plurality of acoustic transducers, each acoustic transducer being configured to transmit and receive acoustic signals; and
a control unit coupled to the array and configured to selectively power a number of the acoustic transducers using standoff distance between the array and a borehole wall.

2. The borehole tool according to claim 1, wherein the control unit is configured to vary frequency of acoustic signals transmitted from the array based upon the standoff distance between the array and the borehole wall.

3. The borehole tool according to claim 2, wherein the frequency of the acoustic signal increases as the standoff distance between the array and the borehole wall decreases.

4. The borehole tool according to claim 3, wherein the control unit varies the frequency of the acoustic signal based upon attenuation of a borehole fluid.

5. The borehole tool according to claim 1, wherein the control unit is configured to power the plurality of acoustic transducers such that the number of transducers selectively powered decreases as the standoff distance decreases.

6. The borehole tool according to claim 1, wherein the control unit is configured to vary timing of transmitted acoustic signals at the plurality of acoustic transducers.

7. The borehole tool according to claim 1, wherein the control unit is configured to vary timing of received acoustic signals at the plurality of acoustic transducers.

8. The borehole tool according to claim 1, wherein the control unit is configured to determine standoff based upon an acoustic signal that is reflected back from the borehole wall.

9. The borehole tool according to claim 1, wherein the array is defined by a circular area and each acoustic transducer forms a ring disposed concentrically within the circular area.

10. The borehole tool according to claim 1, wherein the borehole tool is a logging-while-drilling (LWD) tool.

11. A method for acoustically imaging a borehole wall, the method comprising:
disposing an array including a plurality of acoustic transducers within a borehole;
selectively Dowering a number of the plurality of transducers using standoff distance between the array and the borehole wall to transmit acoustic signals towards the borehole wall.

12. The method according to claim 11, further comprising:
receiving, at the array, an acoustic signal that is reflected back from the borehole wall.

13. The method according to claim 11, further comprising:
selecting a frequency for the acoustic signal transmitted from the array based upon the standoff distance between the array and the borehole wall.

14. The method according to claim 13, wherein the frequency of the acoustic signal decreases as the standoff distance between the array and the borehole wall increases.

15. The method according to claim 13, wherein selecting the frequency for the acoustic signal is further based upon attenuation of a borehole fluid.

16. The method according to claim 11, further comprising:
determining the standoff distance between the array and the borehole wall.

17. The method according to claim 11, wherein the number of selected transducers decreases as the standoff distance decreases.

18. The method according to claim 11, further comprising:

varying timing of the transmitted acoustic signals at the plurality of acoustic transducers.

19. The method according to claim 12, further comprising:

varying timing of the received acoustic signals at the plurality of acoustic transducers.

20. A logging-while-drilling tool comprising:

an array including a plurality of acoustic transducers, each acoustic transducer being configured to transmit acoustic signals; and a control unit coupled to the array and configured to (i) selectively power a number of the acoustic transducers and (ii) vary frequency of acoustic signals transmitted from the array using standoff distance between the array and a borehole wall.

* * * * *